United States Patent [19]

Saleh et al.

[11] Patent Number: 5,403,964
[45] Date of Patent: Apr. 4, 1995

[54] PROCESS FOR CONVERSION OF ETHERS TO ALCOHOLS AND OLEFINS

[75] Inventors: Ramzi Y. Saleh, Flemington; Joel R. Livingston, Jr., Basking Ridge; Michael Siskin, Morristown; Glen B. Brons, Phillipsburg, all of N.J.

[73] Assignee: Exxon Research & Engineering Co., Florham Park, N.J.

[21] Appl. No.: 187,672

[22] Filed: Jan. 27, 1994

[51] Int. Cl.⁶ .................. C07C 27/00; C07C 29/00; C07C 31/10; C07C 31/12
[52] U.S. Cl. .................. 568/907; 568/835; 585/639
[58] Field of Search .................. 568/907, 835

[56] References Cited

U.S. PATENT DOCUMENTS 4,368,337  1/1983  Tawara et al. .................. 568/907
5,043,486  8/1991  Siskin et al. .................. 568/907

OTHER PUBLICATIONS

Schwartz et al "Surface Active Agents" vol. 1 (1949) pp. VII, VIII and 111–126.

*Primary Examiner*—Joseph E. Evans
*Attorney, Agent, or Firm*—Linda M. Scuorzo

[57] ABSTRACT

The present invention relates to enhanced process for converting certain ethers, such as sec-butyl ether and isopropyl ether to their corresponding reaction products in the presence of water. This may be accomplished by adding a rate enhancing surfactant, such as an anionic or cationic surfactant to a mixture of the ether and water, preferably least about $10^{-5}$ molar surfactant. Under those conditions the reaction shows an increase in reaction rate over the rate of the process wherein surfactant is not used.

5 Claims, No Drawings

PROCESS FOR CONVERSION OF ETHERS TO ALCOHOLS AND OLEFINS

FIELD OF THE INVENTION

The present invention relates to an enhanced process for converting certain ethers into reaction products.

DESCRIPTION OF RELATED ART

Various processes are known for converting ethers into mixtures comprising predominantly alcohols and olefins. Ethers are typically an undesirable by-product of a number of commercial processes, e.g., the hydration of propylene with sulfuric acid to form isopropyl alcohol; the synthesis of methyl ethyl ketone involves initial hydration of butylene which also forms substantial quantities of sec-butyl ether. It is currently more economically desirable to produce alcohols and olefins than ethers in many cases, thus commercial processes that achieve this result represent a potential advantage.

U.S. Pat. No. 5,043,486 discloses a process for aquathermolysis of ethers in the presence of water. Applicants have found an enhanced process which increases the reaction rate thus augmenting product yields.

SUMMARY OF THE INVENTION

The invention provides for an enhanced process for converting certain ethers or mixtures of ethers, such as, $C_8$ and smaller ethers, exemplary of which are di-sec-butyl ether ("sec-butyl ether") and di-isopropyl ether ("isopropyl ether") in the presence of water to their corresponding reaction products (e.g., olefins, alcohols and mixtures thereof), by conducting the process in the presence of an effective amount of a rate enhancing surfactant to produce the corresponding reaction products at increased rates. Typically a concentration of about $10^{-5}$ molar surfactant is sufficient.

DETAILED DESCRIPTION OF THE INVENTION

The invention provides for an enhanced process for cleaving one or a mixture of different ethers having the general formula (1) below:

 (1)

wherein n is a whole number ranging from 1 to 4, R and R' may be the same or different and are selected from the group consisting of linear and branched aliphatic groups containing from 1 to 30 carbon atoms and cycloaliphatic groups containing from 3 to about 25 carbon atoms.

Inclusive of such ethers are diethers and triethers where n in formula 1 is greater than 1, such as ethylene glycol dimethyl ether. More preferred diethers include $C_3$ to $C_{10}$ diethers such as trimethyl diether, triethyl diether and so on up to about tridecyl diether. Also included within the scope of the formula are simple monoethers wherein n is 1. Such ethers include branched or linear aliphatic ethers such as methyl ether, methyl ethyl ether, ethyl ether, n-propyl ether, isopropyl ether, sec-butyl ether, methyl n-butyl ether, ethyl n-butyl ether, n-butyl ether, n-amyl ether, isoamyl ether, n-hexyl ether, n-decyl ether and the like. The more preferred monoethers are those wherein R and $R^1$, above contain from 1 to 15 carbon atoms. The process is also applicable to cleavage of ethers containing one or more cycloaliphatic groups such as cyclohexyl alkyl ethers, including cyclohexyl ether, cyclohexyl ethyl ether, cyclohexyl butyl ether and the like.

The terms "aliphatic" and "cycloaliphatic" as used herein are also intended to be inclusive of such groups containing one or more non-interfering substituent groups replacing hydrogen on the carbon chain or ring.

The term "autogeneous pressure of the system" refers to the combined vapor pressure exerted by the mixed components present in the aqueous system heated at a particular process temperature. The autogeneous pressure of water alone in such a system ranges from about 500 psia (66.7 kPa or 3.45 MPa) to 3200 psia (426.6 kPa or 22.06 MPa) over a temperature range of from about 250° C. up to about 374.4° C., the critical temperature of water. Obviously, the autogeneous pressure of a system containing both water and the ether would be higher over this temperature range as a function of the ether content and the resulting partial pressures exerted by the ether.

The terms "conversion", "cleavage" and "hydrolysis" as used herein is defined as carbon-oxygen (C—O) bond cleavages in ethers to produce more desirable value added chemical compounds. Where the starting ethers are aliphatic or cycloaliphatic ethers, the product of the reaction generally comprises a mixture composed primarily of the corresponding alcohol and olefin. For example, cleavage of an alkyl ether such as ethyl ether gives rise to predominantly ethanol and ethylene as a mixed reaction product; cleavage of isopropyl ether gives rise to predominantly isopropyl alcohol and propylene as a mixed reaction product; cleavage of sec-butyl ether gives rise to a mixture of predominantly sec-butyl alcohol and butenes; cleavage of cyclohexyl ethyl ether gives rise to a mixture of predominantly ethanol and 1-methylcyclopentene; and so forth.

As used herein "% conversion", "% selectivity" and "% yield" may be calculated as follows:

% conversion = moles of starting material converted ÷ total moles of start material × 100

% selectivity = moles of desired product ÷ total moles of starting material converted yield = % selectivity × % conversion Disclosed in U.S. Pat. No. 5,043,486 was a process for aquathermolytically cleaving ethers, which disclosure is incorporated herein by reference. By way of summary the features are as follows.

The starting materials used herein may be obtained from commercial sources or synthesized according to known procedures.

The process was conducted by introducing the water and ether into a reaction vessel and heating the mixture under autogeneous pressure and preferably in an inert atmosphere, such as argon or nitrogen, as an aid in excluding oxygen from the system, and at a temperature within the range of from about 250° to 450° C. for a period of time such that at least about 20% by weight of the ether was cleaved or converted into other products. Normally, the process was conducted at a temperature not higher than the critical temperature of water which is about 374° C., but supercritical temperatures above that and up to about 450° C. also were disclosed. Good results in terms of the percentage of ether converted and yield of alcohol realized were disclosed as achievable with process temperatures within the range of from about 300° to 374° C.

Although ordinary tap water may be used in the process, distilled or deionized water substantially free of dissolved salts were preferred and particularly preferred was to use water which had been deoxygenated and was substantially free of dissolved oxygen, in order to minimize the occurrence of free radical side reactions during the process.

The amount of water used in forming the mixture with the ether generally ranged from at least about 50% by weight up to about 97% by weight, i.e., the mixture could have contained from about 1 to 30 parts by weight water per part by weight ether. It was disclosed that the higher the water content of the mixture within the above specified range, the greater the conversion of the ether at any given process temperature within the 250° to 450° C. range.

Conversely, it was disclosed that the higher the process temperature within that range, the less water was required to give rise to higher conversion rates of the ether. The preferred water content of the mixture ranged from about 2 to about 15 parts by weight per part by weight ether, with 2 to 10 parts by weight being most preferred.

Acceptable levels of ether conversion of at least about 20% were disclosed in U.S. Pat. No. 5,043,486 achieved by conducting the reaction over a time period of as little as 5 minutes up to 120 minutes or more. At higher temperatures and/or with higher water/ether ratios, less time was disclosed as required to achieve good ether conversion and vice versa. Most preferably the water content and reaction temperatures were such as to achieve ether conversions of at least about 30% within 10 to 60 minutes, more preferably within 10 to 30 minutes.

It was disclosed as not necessary and indeed undesirable to include added catalyst components in the reactant mixture in the process.

U.S. Pat. No. 5,043,486 also indicated that the reaction mixture may include small quantities of an ionic surfactant stable at higher temperatures to assist in enhancing the dispersibility of the ether in the water, particularly where higher molecular weight ethers were present.

Unexpectedly, Applicants have discovered that certain surfactants when added to the reaction mixture of water and an ether or mixture of ethers have a rate enhancing effect on the process. This is even more surprising in the case of lower molecular weight ethers because one skilled in the art would consider a surfactant unnecessary in those cases because the ethers are completely miscible or soluble in the water under the reaction conditions.

The unexpected rate enhancing effect may be seen by an increased conversion to the corresponding reaction products (e.g., of ether to alcohol and/or olefin) in a given unit of time in comparison to the reaction when conducted in the absence of an added surfactant. This result is particularly desirable because the increase in rate may be used to produce an increase in conversion of ether to products in a given time, e.g., alcohol and olefin, when the surfactant is present in comparison to the process carried out with water and ether alone, i.e. without the added surfactant. Such an increase in rate is economically attractive due to the increase in productivity per reactor volume (i.e., uses less reactor volume). Table 1 demonstrates this result by comparing the percent conversion of the prior art process, U.S. Pat. No. 5,043,486, Table 1 Example 9 for isopropyl ether, and U.S. Pat. No. 5,043,486, Table 1 Example 24 for sec-butyl ether), with the process of the present invention which is carried out in the presence of a number of different rate enhancing surfactants. The result is particularly noticeable when the process includes ethers that are sufficiently water soluble or miscible at reaction conditions so as not to require the presence of a surfactant in order to achieve or enhance dispersibility in water. By way of example these include $C_8$ and smaller ethers, such as sec-butyl and isopropyl ether, more suitably $C_4$ and smaller ethers.

In the present invention the surfactants are rate enhancing surfactants, i.e. surfactants present in an effective amount to result in an increased rate of conversion of the ether to the corresponding products (typically alcohol, olefin and mixtures thereof) as compared to that produced in the absence of a surfactant, using water and a ether starting material alone. Surfactants should be chosen that are thermally stable at process conditions. While it is expected that for less thermally stable surfactants some surfactant decomposition may occur at process conditions, this should be minimized by choice of the appropriate surfactant.

For higher molecular weight ethers, that are not as soluble in hot water, e.g., above $C_8$ and higher, the surfactant provides the unexpected rate enhancing benefit that also is seen with respect to lower molecular weight ethers but also assists in enhancing the solubility of the ether in water and should be chosen with a view toward enhancing solubility in order to provide optimal reaction conditions. Generally, surfactants are preferred that not only function as effective rate enhancers, but also provide the needed thermal stability at process conditions.

The amount of surfactant should be a rate enhancing amount, typically a concentration of at least about $10^{-5}$ molar, preferably at least about $10^{-3}$ molar based on the weight of the water solution.

However, some surfactants, particularly salts, show decreased solubility particularly at temperatures above the critical temperature of water, 374.4° C., and thus when these are used, temperatures should be effective to maintain surfactant solubility at reaction conditions.

In appropriate cases it may be desirable to also add small quantities of a stronger or weaker acid to the reaction mixture, since it has been found that the presence of the acid enhances the ionic reaction mechanism and generally gives rise to even higher rates of conversion of the ether starting material.

The inventions disclosed herein may suitably comprise, consist, or consist essentially of the elements disclosed herein.

In the preferred embodiment of the present invention, the reaction mixture "consists of" a mixture of water, ether and a rate enhancing surfactant.

In a second embodiment the reaction mixture may also "consist essentially of" a mixture of water, ether and surfactant and may further include less than 3% by weight of stronger or weaker acid component sufficient to develop a weakly acidic aqueous mixture having a pH within the range of from about 3.5 up to about less than 7 at room temperature.

The addition of stronger acids such as sulfuric, hydrochloric, or phosphoric to the aqueous reaction media at levels of less than about 0.5% by weight gives rise to higher ether conversion rates but tends to disfavor selectivity toward the yield of alcohols and favor selectivity toward the production of olefins or other by-products. In partial contrast, the addition of weaker acids such as acetic acid or finely divided aluminosilicate materials to the aqueous reaction medium at levels of less than about 3% by weight also tends to give rise to higher ether conversion rates, but greater selectivity toward the yield of alcohols. Thus, the process may be further modified by the inclusion of acidic materials in the reaction media to enhance ether conversion and influence selectivity towards the production of alcohols on the one hand or other by-products on the other hand, depending on the identity, strength and concentration of the acid.

Since the process produces lower molecular weight alcohol and olefin cleavage or reaction products as compared to the molecular weight of the starting ether, and these cleavage products typically have increased solubility in water, they tend to compensate for surfactant loss due to degradation or decomposition and typically enhance the solubility of the remaining materials. Factors such as increased solubility of the ethers in the liquid water help facilitate ionic reaction pathways in the aqueous system and thus are very desirable.

Examples of preferred anionic surfactants include prefluorinated anionic surfactants such as perfluorocarboxylic acids. Other preferred surfactants include sodium and potassium salts of straight chain ($C_8$ to $C_{20}$) fatty acids and linear alkyl-benzene sulfonates, toluene sulfonates, xylene sulfonates, naphthalene sulfonates and ligninsulfonates, mainly sodium, calcium and amine salts having the alkyl group of from about 8 to 14 carbon atoms.

Examples of preferred cationic surfactants include primary amines derived from animal and vegetable fatty acids, tall oil, synthetic $C_{12}$ to $C_{18}$ primary, secondary, and tertiary amines, diamines and polyamines and their salts, such as N-alkytrimethylene diamine salts and N-alkylimidazolines. Quaternery ammonium salts have the advantage that the positive charge remains in acidic, neutral, and alkaline media. Examples include dimethylammonium chloride and N-alkylmethylammonium chlorides. Polyoxyethylenated long chain amines, $RN[(CH_2CH_2O)_xH]$ combine increased water solubility with cationic characteristics of the amino group. Quaternized polyoxyethylenated long chain amines, $RN(CH_3)[(C_2H_4O)_xH]_2+Cl-$, and amine oxides such as N-alkyldimethylamine oxides are acceptable. The latter form 1:1 salts with anionics that are much more surface active than either the anionic or the amine oxide.

The percent conversion of starting ethers which may be achieved in accordance with the improved process of this invention may generally range from at least about 40% up to 100%, depending upon reaction conditions, and the selectivity of the process toward the production of alcohols may generally range from about 20% up to about 65% or more, once again depending on reaction conditions. The process may be tailored within the process parameters described herein to balance maximum conversion of the starting ether with favorable selectivity toward the desired reaction product, whether it be alcohol, olefin, or other achievable reaction products.

The process of the present invention may be particularly adapted for use in conjunction with other chemical processes wherein ethers are formed as a less valuable by-product, including processes as are generally described in the Background section of the disclosure. For example, alcohols may be prepared commercially by the hydration of olefins with a strong acid such as sulfuric acid, and the reaction product invariably contains some quantity of an aliphatic or cycloaliphatic ether derived from the olefin. These ethers may be readily separated from the alcohol mixture by distillation or other conventional separation techniques, and subjected to the present process to produce additional alcohol and olefin. The olefin may then be readily separated from the reaction mixture and recycled to the main process for further production of alcohol, or may be removed for other uses. The advantageous use of the present process in conjunction with other chemical processes where ethers are formed as by-products should be evident to the skilled practitioner.

The process of this invention may be carried out batchwise or in the continuous mode using conventional pressure equipment. Examples of such equipment includes a laboratory bomb, a high pressure autoclave, a stirred tank reactor or a continuous flow-through tube, each equipped with a heating means capable for achieving and maintaining the required temperatures and pressures over the required time period.

The following examples are illustrative of the invention.

EXAMPLES

All materials except those indicated were obtained from commercial sources and used without further purification. The reactions summarized in Table 1 were carried out in liquid water at 315° C. for the time period indicated, in a T-316 stainless steel reactor bomb having a capacity of 11 cc. The reactor was sealed under argon and the reaction mixture was heated in the sand bath. The reactor was then cooled to room temperature. The reaction mixture was then extracted with diethyl ether. Table 1, Run 1 corresponds to Example 9 in U.S. Pat. No. 5,043,486, which represents the baseline prior art process using water and isopropyl ether alone. Comparison of the results for the baseline to Runs 2 through 3 demonstrates the increase in rate of producing reaction product in the presence of the surfactant as evidenced by an increase in percent conversion of isopropyl ether to about 85% alcohol and olefin for Applicants' process under the same reaction time and conditions. Table 1, Run 4 corresponds to Example 24 in U.S. Pat. No. 5,043,486, which represents the baseline prior art process using water and sec-butyl ether alone. Comparison of the results for the baseline to Runs 6 through 11 demonstrates the increase in rate of producing reaction products in the presence of rate enhancing surfactants as evidenced by an increase in percent conversion of sec-butyl ether for Applicants' process at the same reaction time and conditions. In each case, a 5%(w/w) mixture of the water to ether was used and surfactant concentration was 0.001M in water. Isopropyl ether ("IPE") used was 99% pure. Reagent grade sec-butyl ether ("SBE-R") was 99% pure, while Exxon grade sec-butyl ether ("SBE-Ex") was 62.8% sec-butyl ether, with the remainder essentially branched octenes. As used in the Table 1 "DBSA-MEA" means dodecyl benzene sulfonic acid neutralized with monoethanol amine to pH 8.5. "DBSA-Na" means the sodium salt of DBSA. "PTSA-Na" means the sodium salt of p-toluene sulfonic acid.

TABLE 1

AQUATHERMOLYTIC CLEAVAGE OF ETHERS-EFFECT OF SURFACTANTS

| Run No. | Medium | Surfactant | Reaction Time | % Conversion |
|---|---|---|---|---|
| 1 | $H_2O$/IPE | None | 10 min. | 52 |
| 2 | $H_2O$/IPE | DBSA-MEA | 10 min. | 87 |
| 3 | $H_2O$/IPE | DBSA-MEA | 10 min. | 83 |
| 4 | $H_2O$/SBE-R | None | 30 min. | 63 |
| 5 | $H_2O$/SBE-Ex | None | 30 min. | 59 |
| 6 | $H_2O$/SBE-R | DBSA-MEA | 30 min. | 99 |
| 7 | $H_2O$/SBE-Ex | DBSA-MEA | 30 min. | 96 |
| 8 | $H_2O$/SBE-R | DBSA-Na | 30 min. | 75 |
| 9 | $H_2O$/SBE-R | DBSA-Na | 30 min. | 70 |
| 10 | $H_2O$/SBE-Ex | DBSA-Na | 30 min. | 66 |
| 11 | $H_2O$/SBE-R | PTSA-Na | 30 min. | 64 |

What is claimed is:

1. A process for converting ethers to the corresponding reaction products, consisting essentially of: heating an aqueous mixture of water soluble $C_8$ and smaller ethers and water, at reaction conditions of from about 200° C. to about 450° C., in the presence of a rate enhancing amount of at least about $10^{-5}$ molar surfactant for a time sufficient to produce mixtures containing the corresponding reaction products at a rate greater than in the absence of the surfactant.

2. The process of claim 1 wherein the ether is selected from the group consisting of sec-butyl ether, isopropyl ether and mixtures thereof.

3. The process of claim 1 wherein the surfactant is selected from the group consisting of anionic and cationic surfactants.

4. The process of claim 1 wherein the surfactant is present in a concentration of at least about $10^{-3}$ molar.

5. The process of claim 1 wherein the surfactant is selected from the group consisting of dodecyl benzene sulfonic acid neutralized with monoethanol amine, sodium salt of dodecyl benzene sulfonic acid, and the sodium salt of p-toluene sulfonic acid.

* * * * *